(12) United States Patent
Orgel et al.

(10) Patent No.: US 10,336,814 B2
(45) Date of Patent: *Jul. 2, 2019

(54) METHOD FOR OBTAINING THIN FIBRIL COLLAGEN BY CONTACTING NATIVE COLLAGEN WITH AN ANTIBODY

(71) Applicant: MATRIX ODYSSEY, LLC, Northbrook, IL (US)

(72) Inventors: Joseph Orgel, Northbrook, IL (US); Olga Antipova, Naperville, IL (US)

(73) Assignee: MATRIX ODYSSEY, LLC, Northbrook, IL (US)

( * ) Notice: Subject to any disclaimer, the term of this patent is extended or adjusted under 35 U.S.C. 154(b) by 57 days.

This patent is subject to a terminal disclaimer.

(21) Appl. No.: 15/257,089

(22) Filed: Sep. 6, 2016

(65) Prior Publication Data

US 2016/0368968 A1 Dec. 22, 2016

Related U.S. Application Data

(63) Continuation of application No. 12/419,689, filed on Apr. 7, 2009, now Pat. No. 9,458,224.

(51) Int. Cl.
| | |
|---|---|
| *C07K 14/78* | (2006.01) |
| *G01N 33/68* | (2006.01) |
| *A61L 27/24* | (2006.01) |
| *C07K 1/14* | (2006.01) |

(52) U.S. Cl.
CPC .............. *C07K 14/78* (2013.01); *A61L 27/24* (2013.01); *C07K 1/14* (2013.01); *G01N 33/6887* (2013.01); *A61L 2430/40* (2013.01); *G01N 2333/78* (2013.01)

(58) Field of Classification Search
CPC ........... C07K 14/78; C07K 1/14; A61L 27/24; A61L 2430/40; G01N 33/6887; G01N 2333/78
See application file for complete search history.

(56) References Cited

U.S. PATENT DOCUMENTS 9,458,224 B2 * 10/2016 Orgel et al. ............ C07K 14/78

OTHER PUBLICATIONS

Kelly ET J. et al., "Fibril-forming Collagens in Lamprey", The Journal of Biological Chemistry, Jan. 15, 1988, vol. 263, No. 2, pp. 980-987. (Year: 1988).*
Cole et al., "Further Effects of Animal Age on the Alkali Process Gelatin Manufactured From Bovine Hide", Proc. Centinary Conf. Int. Union of Leather Technologists and Chemists, 1997, 9 pages.
Kavanagh et al., "Distribution of Biglycan and Decorin in Collateral and Cruciate Ligaments and Menisci of the Rabbit Knee Joint", J. Histochem. Cytochem. 49:877-885, 2001.
Corsi etal., J. Bone Min. Res. 17:1180-1189, 2002.
Campbell et al., Mol. Cell. Biomech. 5:27-36, 2008.
Tomiosso et al., Biocell 29:47-54, 2005.
Risbud et al., Trends Biotechnol. 20:351-356, 2002.
Badylak, Cell Develop. Bioi. 13:377-383, 2002.
Ekman et al., Vet. Pathol. 29:514-520, 1992.
Mosher, D. F., et al. "Assembly of extracellular matrix," Curr. Opln. Cell B1ol., vol. 4 No. 5, 1992), pp. 810-818 (the year of publication is sufficiently earlier than the effective U.S. filing date so that the particular month of publication is not an issue).
Prockop, D.J. et al., "Collagens: molecular biology, diseases, and potentials for therapy," Annu. Rev. Biochem., (1995) 64, pp. 403-434 (the year of publication is sufficiently earlier than the effective U.S. filing date so that the particular month of publication is not an issue).
Sheren et al., "Type II collagen of lamprey," Comp. Biochem Physiol., vol. 85B, No. 1, 1986, pp. 5-14 (the year of publications is suffciently earlier than the effective U.S. filing date so that the particular month of publication is not an issue).
Kadler, K.E., "Extracellular matrix 1. Fibril-forming collagens," Protein Profile, vol. 2, No. 5, (1995), pp. 491-619 (the year of publication is suffciently earlier than the effective U.S. filing date so that the particular month of publication is not an issue).
Polgar, A., et al.., "Elevated levels of synovial fluid antibodies reactive with the small proteoglycans biglycan and decorin in patients with rheumatoid arthritis or other joint diseases." Rheumatology vol. 42, Feb. 28, 2003, pp. 522-527.
Mitchell, P.G. et al. "Cloning, expression and type II collegenolytic activity of matrix metalloproteinase-13 from human osteoarthritic cartilage," J. Clin. Biol. vol. 97 No. 3, Feb. 1996, pp. 761-768.
Ameye L. et al., "Anbormal collagen fibrils in tendons of biglycan/fibromodulin-deficient mice lead to gait impairment, ectopic ossification, and osteoarthritis," FASEB J., vol. 16, May 2002, pp. 673-680.
Scott P.G. et al., "Isolation and characterization of small proteoglycans from different zones of the porcine knee meniscus," Biochem. Biophys. Acta. 1336.2, Aug. 29, 1997, pp. 254-262.
Perumal, S. et al. "Collagen fibril architecture, domain organization, and triple-helical conformation govern its proteolysis," Proc. Natl. Acad. Sci. U.S.A., Feb. 26, 2008, vol. 105 No. 8, pp. 2824-2829.
Orgel, J.P. et al., "Microfibrillar structure of type I collagen in situ.", Proc. Natl. Acad. Sci. U.S.A., Jun. 13, 2006, vol. 103 No. 24, pp. 9001-9005.
Antipova, "The Studies of Collagen Type II Macromolecular Structure by X-Ray Fiber Diffraction and Electron Microscopy Techniques" PhD Thesis for IIT Dept. of Biol. Chern. and Phys. Sci., Dec. 2007. 187 pages.
Jiang et al., J. Struct. Bioi. 148:268-278, 2004.
Holmes et al.; The 10+4 microfibril structure of thin cartilage fibrils; PNAS; Nov. 14, 2006; vol. 103, No. 46; pp. 17249-17254.

(Continued)

*Primary Examiner* — Satyendra K Singh
(74) *Attorney, Agent, or Firm* — K&L Gates LLP

(57) ABSTRACT

A collagen material having a form of thin fibrils generally free of fibril-bundling proteogylcan interactions, and a method for providing the thin fibril collagen material from native collagen fibers. The method uses proteoglycan antibodies to disassociate the proteoglycan interactions in bundled collagen fibrils to provide the constituent fibrils. The process can be used as a model for arthritis and the resulting fibrils can be used to form new extracellular matrix biomaterials and new tissues.

9 Claims, 3 Drawing Sheets

Specification includes a Sequence Listing.

(56) References Cited

OTHER PUBLICATIONS

Antipova et al.; Non-Enzymatic Decomposition of Collagen Fibers by a Biglycan Antibody and a Plausible Mechanism or Rheumatoid Arthritis; PLoS ONE; Mar. 2012; vol. 7; Issue 3; pp. 108.
Orgel et al.; Molecular and structural mapping of collagen fibril interactions; Connective Tissue Research 52(1) pp. 2-17 (2011).
Eikenberry et al.; Crystalline Fibril Structure of Type II Collagen in Lamprey Notochord Sheath; 1984; J. Mol. Biol. (1984) 176; pp. 261-277.

* cited by examiner

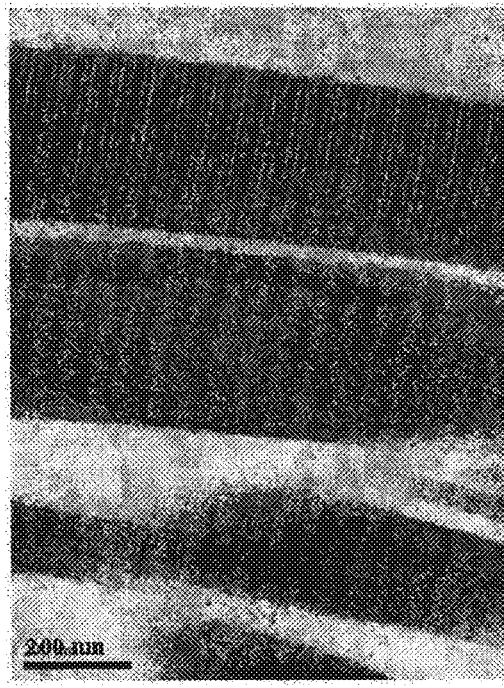
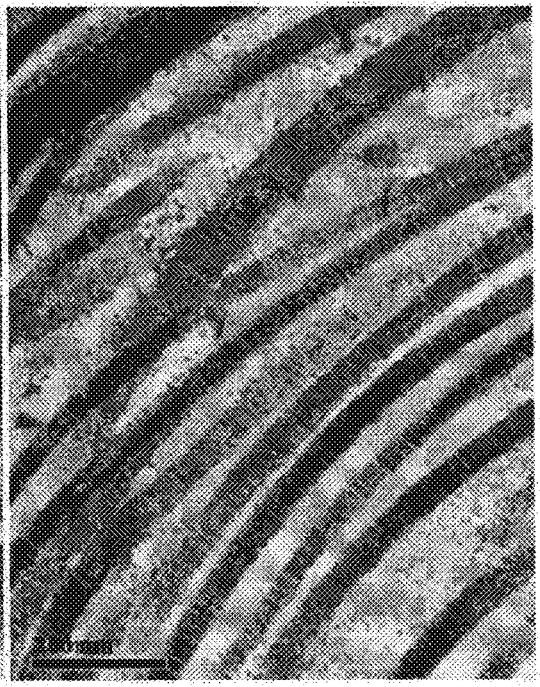
FIG. 1        FIG. 2
FIG. 3

METHOD FOR OBTAINING THIN FIBRIL COLLAGEN BY CONTACTING NATIVE COLLAGEN WITH AN ANTIBODY

PRIORITY CLAIM

This application is a continuation of U.S. patent application Ser. No. 12/419,689 filed Apr. 7, 2009, the entire contents of which are incorporated herein by reference.

This invention was made with government support under award 0644015, awarded by National Science Foundation. The government has certain rights in the invention.

BACKGROUND OF THE INVENTION

This invention relates generally to a collagen material having a form of thin fibrils and a method for obtaining fibril collagen and, more particularly, to a process that reduces native type II collagen fibers into their constituent thin fibrils.

The collagens are fibrous proteins found in all multicellular animals. Collagens are the major component of skin, bones, cartilages, teeth, tendons and other extracellular matrixes (ECM). Collagen is the most abundant protein in mammals (about 25% to 30% of total protein mass). The major collagen types are types I, II, III, V, and XI (collectively 80-90% of all collagen in the body). Collagen molecules are about 300 nm long with rather short nonhelical regions at both ends (N- and C-telopeptides). The collagen molecules form fibers of different size and diameter. Negative and positive staining shows that collagen types I, II, and III each have fiber periodic bands of about 67 nm (Mosher, D. F. et al., "Assembly of extracellular matrix," *Curr. Opin. Cell Biol.* 4.5 (1992): 810-818), which correspond to their complicated macromolecular structure.

Collagen is a crucial structural component of almost all connective tissues, and its three-dimensional molecular packing structure and microfibrillar and fibrillar structures are crucial aspects of the proper function of animal tissues. Collagen type II is a major component of articular cartilage, bones, notochord, vitreous humour and other cartilage-like tissues. The type II collagen molecule is a homotrimer with three identical α1 chains, coded by a single gene; each of them is 1060 amino acid residue long after the cleavage of their pro-peptides. Prockop, D. J. et al., "Collagens: molecular biology, diseases, and potentials for therapy," *Annu. Rev. Biochem.* 64 (1995): 403-434. It has a triple helical region about 300 nm long and short nonhelical N- and Ctelopeptides, the triple helix diameter is approximately 1.4 nm and collagen molecular weight is about 285 kDa. The sequence of collagen type II has been identified for some species such as humans (ExPASy sequence data bank code P02458). Sea lamprey (*Petromyzon marinus*) notochord is a particularly useful source of collagen for structural characterization of collagen molecules and fibrils, due to the fact that collagen packing in the lamprey is relatively crystalline in its notochord relative to that of other animal tissues. The fact that lamprey collagen type II fibrils appear to be indistinguishable from mammalian cartilage as judged by its amino acid staining pattern viewed via TEM (Sheren et al., "Type II collagen of lamprey", *Comp. Biochem Physiol B* 85 (1986): 5-14), whilst being organized in a more simplistic manner indicates the tissues usefulness as a model system for mammals. Although the amino acid sequence of collagen type II of sea lamprey is not fully established (only the C-terminal half), it is apparent from TEM data that any differences in the N-terminal half are likely to be trivial (see above). In addition, unlike collagen type I, collagen type II is highly homologous between species. Kadler, K. E., "Extracellular matrix. Fibril-forming collagens," *Protein Profile* 2 (1995): 491-619.

Collagen type II molecules are known to form fibrils (which may be made from microfibrils) which bundle to form fibers and can be visualized by microscopy techniques. The type II fibers are different from those of type I collagen, and the higher structures they form can vary between the tissues and species, depending on the particular ECM content. The collagen type II microfibril is believed to be a super coil of five collagen molecules, which is the same as type I collagen, but their fibillar structures are significantly different. Collagen type II fibers are found in cartilage, bones, intervertebral discs, inner ear, vitreous humour, dermis, and notochord. The fibers in these tissues are formed by collagen type II with the participation of other ECM molecules (collagen-ligands) produced by tissue-specific cells. The interaction of the collagen-ligands with collagen influences the size of the fibrils/fibril bundles and their aggregate fibers and meshwork in the tissues. Among these tissue types, lamprey notochord and bovine articular cartilage, for example, contain more collagen type II than any other collagen type, and their aggregates are rather large.

Notochord, a characteristic tissue of chordates, is a cartilage-like tissue that spans the length of the chordate back, located beneath and parallel to the central nervous system between the brain and tail. This tissue is composed of cells embedded in a fibrous sheath, which is in turn composed primarily of collagen, and has a roughly cylindrical shape. Although it is the main axial skeleton at the embryonic stage, the notochord is replaced by the vertebral column in most vertebrates. However, in some chordates it remains into adulthood (e.g., lamprey, lungfish, sturgeon, and some sharks). The mature notochord contains a soft cellular inner part, surrounded by protective fibrous sheath, composed of three layers: inner basal lamina, thick collagenous (cartilage-like) layer, and elastic filamentous membrane. The collagenous part of the notochord has two main fiber orientations: circular (perpendicular to the main body axis) and longitudinal (parallel to the main axis of the body). Longitudinally organized fibers are located at the outer layer and are the most prevalent. The notochord cylindrical structure gives the body flexibility and support; it also serves as an attachment anchor for segmental muscles and plays a role in cellular-signaling and endodermal structure development.

Cartilage is the main collagen type II containing tissue in the body. There are three major types: 1) elastic cartilage, 2) fibrocartilage, and 3) hyaline cartilage. Elastic cartilage is found in the epiglottis and the eustachian tube. Fibrocartilage often exists temporarily at fracture sites and permanently in the intervertebral disks of the spine, at the mandibular condyle covering in the temporomandibular joint, and in the meniscus of the knee. The hyaline cartilage, also known as articular cartilage, is mostly found in diarthroidal joints covering long bones and it also forms the growth plate for long bones.

Resilient articular cartilage distributes mechanical load and protects the bones from stress. Cartilage dry weight is predominantly collagen type II (stretch resistance) and proteoglycans/GAGs (conveying compression resistance and/or stabilization of fibril-bundle structures). There are also other collagens (types III, IX and XI) and other ECM molecules in cartilage, but in relatively small amounts. Water molecules, organized by proteoglycans in the cartilage meshwork, occupy about 70% of total tissue weight. The main ECM molecules of articular cartilage after collagen type II are dermantan sulfate proteoglycans (DSPGs) (e.g., decorin, biglycan), chondroitin sulfate proteoglycans (CSPG) (e.g., decorin), keratin sulfate proteoglycans (KSPGs) (e.g., aggrecan) and cartilage oligomeric matrix protein, which are involved in collagen network formation and also give the tissue compression resistance, accumulating and holding large amounts of water. The interactions between these compounds and collagen type II are of great interest, due to their relevance to diseases such as osteoarthritis and rheumatoid arthritis.

Rheumatoid arthritis (RA) is a severe disease. The immune system attacks the ECM of joints and causes degradation of articular cartilage. Elevated levels of several antibodies against cartilage ECM components have been detected in serum and synovial fluid of RA patients. However the exact role of these antibodies in initiation and development of the drastic changes in cartilage remains unclear as does the mechanism of tissue destruction. Elevated levels of biglycan antibodies have been detected in the fluids of arthritis patients. Polgar, A. et al., "Elevated levels of synovial fluid antibodies reactive with the small proteoglycans biglycan and decorin in patients with rheumatoid arthritis or other joint diseases." Rheumatology 42 (2003): 522-527. They are considered to be earlier markers of this disease, and in addition, the presence of collagen type II fibers with irregular diameter and high concentration of collagen cleavage products are also connected to arthritis events. Mitchell, P. G. et al., "Cloning, expression, and type II collagenolytic activity of matrix metalloproteinase-13 from human osteoarthritic cartilage," *J. Clin. Biol.* 97.3 (1996): 761-768; and Ameye L. et al., "Abnormal collagen fibrils in tendons of biglycan/fibromodulin-deficient mice lead to gait impairment, ectopic ossification, and osteoarthritis," *FASEB J* 16(2002):673-680.

There is an ongoing need for additional information on the mechanisms of RA and its effect on collagen in joint tissues. There is a need for a RA model for further study and there is a need for means to rebuild or repair collagen-based ECM in RA patients.

SUMMARY OF THE INVENTION

This invention includes thin fibril collagen and a method for obtaining fibril collagen. In one embodiment of this invention, the method of this invention provides the base constituent aggregate of type II collagen monomers: thin fibrils from native mammalian and piscine tissues. The process itself can be used as an in vitro model of part of the pathology of rheumatoid arthritis and offers an in vitro model to study the disease pathology. The method also provides a relatively gentle chemical mechanism to reduce native connective tissues, such as are composed primarily of type II collagen, into a state that can be used to then construct alternate tissue structures for therapeutic use or as scaffolds for tissue seeding or organogenesis.

A general object of the invention can be attained, at least in part, through a method of obtaining thin fibril collagen. The method comprises providing collagen fibers and treating the collagen fibers with an antibody to obtain the thin collagen fibrils. The invention further comprehends a collagen material, such as made by the method of this invention, including collagen fibrils having a width of about 11 to about 17 nanometers.

The antibodies used in the method of this invention attach to biglycan molecules on the collagen fiber surface, and this interaction disrupts the association between biglycan and collagen molecules, presumably by inducing conformational changes in the biglycan protein core. Without the inter-fibril stabilization of biglycan, the fibril bundle ('thick-fibril') forming the collagen fibers disassociates into the constituent thin fibrils of this invention. Unlike the fibril bundles of the fibers, the constituent thin fibrils are not internally stabilized by proteoglycans. The resulting fibrils are aggregates of collagen molecules held together by electrostatic interactions and lysine-hydroxylysine intermolecular cross-links, and hence are not caused to break down further due to the antibody.

The resulting thin fibrils of this invention can be used to form new extracellular matrices (ECM) or new tissue, such as a cartilage tissue. The ECM provides structural support, storage of some essential biomolecules and connection between the cells of multicellular organisms. It generally contains three major types of molecules: structural insoluble proteins (e.g., collagens and elastin), specialized proteins (e.g., fibrillin, fibronectin, and laminin) and proteoglycans (e.g., decorin, aggrecan, etc). As a part of the ECM, collagen interacts with other molecules essential for proper fibril formation, long-term stabilization (proteoglycans, fibronectin, COMP) and turnover (Matrix MetalloProteinases MMPs). In one embodiment of this invention, the new ECM and/or tissue can be formed by the addition of biglycan, decorin, fibronectin, aggrecan, polyethylene glycol, or combinations thereof to the thin fibril collagen.

Proteoglycans are complex molecules containing a protein core and glycoseaminoglycan (GAG) chains, which are covalently linked to the core. GAGs are unbranched polysaccharide chains made of disaccharide units repeats. One of the sugars in this unit is always an amino sugar (e.g., N-acetilglucosamine or N-acetilgalactosemamine), which may also be sulfated. Most GAGs (e.g., not hyaluronan) attach to the core protein to form the proteoglycans. Core protein is synthesized by membrane bound ribosome and transferred into the endoplasmic reticulum lumen. The polysaccharide chains are assembled on the core protein (attached to serine side chain) in the Golgi apparatus. The difference between proteoglycans and glycoproteins is in the quantity and arrangement of their side chains. Proteoglycans contain at least one long (80 sugars) unbranched GAG chain (up to 95% by weight), whereas glycoproteins have 160% carbohydrates by weight, but they are short, branched oligosaccharides. Proteoglycans can be small with one GAG chain (decorin) or two GAG chains (biglycan) and relatively large with over hundred GAG chains (aggrecan).

The proteoglycans and GAGS interaction with other ECM molecules, especially with fibrous proteins, plays a significant role in tissue organization and turnover. Biglycan and decorin bind to collagens at particular sites and regulates the fibril formation. Other interactions also influence the meshwork assembly, cell adhesion, and matrix turnover.

The glycoprotein fibronectin is a fibrous noncollagen component of the vertebrate ECM. It exists in both soluble and fibrillar forms and is involved in various interactions with other matrix molecules playing a great role in matrix organization and cell adhesion. Fibronectin contains two large subunits, connected by disulfide bonds at the C-terminus. Each of them has functionally distinct domains, composed of small modules, with flexible polypeptide chains between them. Fibronectin interacts with other ECM molecules, like collagen type I and II, integrin, heparin, etc.

Other objects and advantages of this invention will be apparent to those skilled in the art from the following detailed description taken in conjunction with the appended claims and drawings.

BRIEF DESCRIPTION OF THE DRAWINGS

FIGS. 1-6 are TEM images of collagen fibers or collagen fibrils obtained according to one embodiment of this invention.

DETAILED DESCRIPTION OF THE INVENTION

Figures 4, 5:
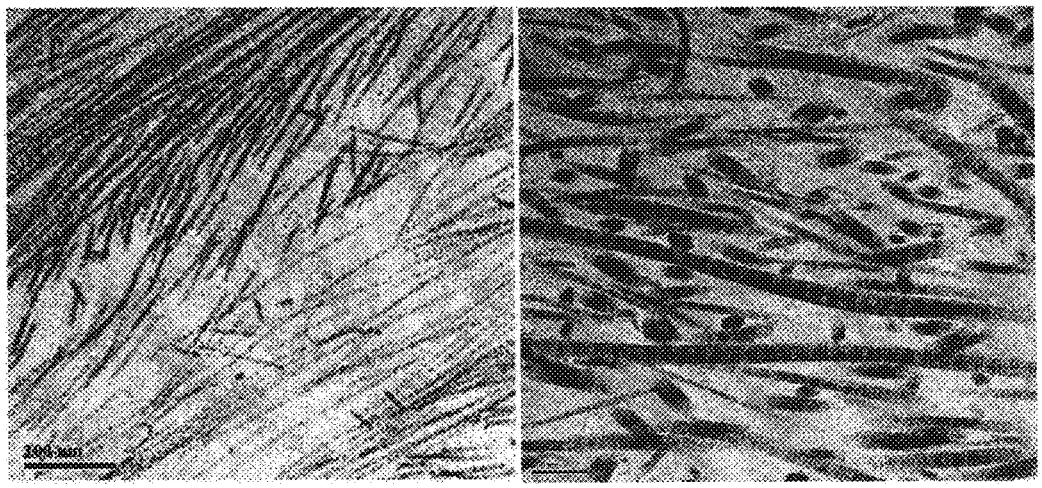

The present invention includes thin fibril collagen and provides a method for obtaining the fibril collagen. In one embodiment of this invention, the method of obtaining thin fibril collagen includes starting with collagen fibers and treating the collagen fibers with an antibody to obtain the desired thin collagen fibrils therefrom. The method of this invention uses proteoglycan antibodies to remove proteoglycans from the collagen fibers, thereby providing the base constituent aggregate of type II collagen monomers—thin fibrils from native mammalian and piscine tissues. References to "native" are to be understood to refer to a naturally occurring operational and/or functional form of a tissue or tissue component. The method of this invention can be used as an in vitro model of part of the pathology of rheumatoid arthritis and offers an in vitro model to study the disease pathology. The method of this invention also provides a relatively gentle chemical mechanism to reduce native connective tissues composed primarily of type II collagen into a state that can be used to then construct alternate tissue structures or other useful bio-materials for therapeutic and other uses, whilst keeping the essential building blocks (the fibrils) intact.

Collagens are the major component of skin, bones, cartilages, teeth, tendons and all other extracellular matrixes (ECM). Collagen type II is the major component of articular cartilage, bones, notochord, vitreous humour and other cartilage-like tissues. Collagen type II molecules are known to form fibrils which bundle to form fibers. The fibers are formed by collagen type II fibrils with the participation of other ECM molecules such as biglycan and decorin. The interactions with collagen influence the size of the fibrils and their aggregate fibers and meshwork in the tissues. Mammalian articular cartilage contains both biglycan and decorin and other ECM molecules, which regulate fibrilogenesis, fiber diameter, support fibers, and give the tissue specific mechanical properties. Cartilage contains more biglycan than decorin although the ratio is different across each specific structural zone. The superficial zone contains about 32% of decorin and 38% of biglycan of all proteoglycan content, the inner deep zone contains about 23% of decorin and 53% of biglycan, and the middle zone has 28% of decorin and 52% of biglycan Scott P. G. et al., "Isolation and characterization of small proteoglycans from different zones of the porcine knee meniscus," *Biochem. Biophys. Acta.* 1336.2 (1997): 254-262.

In one embodiment of this invention, the antibodies attach to at least biglycan molecules of the collagen fiber surface and reduce or remove an amount of biglycan from the collagen fibers. This interaction between the antibodies and the collagen fibers disrupts the association between biglycan and the collagen molecules, presumably by inducing conformational changes in the biglycan protein core. Without the inter-fibril stabilization of biglycan, the fibril bundle forming the fiber (e.g., ~35-50 nm in diameter) reduces in size by disassociating into thin-fibrils, such as fibrils having a diameter of about 12 nm in diameter. Unlike the fibril bundles of the native collagen fibers, these thin-fibrils are not internally stabilized by proteoglycans, but instead are aggregates of collagen molecules held together by electrostatic interactions and lysine-hydroxylysine intermolecular cross-links, and hence are not caused to break down further due to the antibody.

The antibody in one embodiment of this invention is desirably an antibiglycan antibody that when applied to the native collagen fibers, divides the collagen fibers into the constituent fibrils. One particularly preferred anti-biglycan antibody has the antibody epitope of SEQ ID NO: 1, namely DRLAIQFGNYKK. The use of the anti-biglycan antibody is particularly useful for native type II collagen fibers, which have relatively high biglycan content. In other collagen materials, different antibodies can be used depending on the major component proteoglycan.

In one embodiment of this invention, the native collagen fibers are obtained from one or more tissues of an animal. The tissue is desirably mechanically homogenized, sonicated, and/or centrifuged according to practices known to those skilled in the art. The tissue can optionally be denatured, such as by using, for example, guanidine hydrochrolide, which denatures most, if not all, tissue components and molecules except collagen. These procedures can additionally or alternatively be performed after the antibody treatment to ensure a more complete separation of the thin fibrils from the remaining tissue material. Centrifugation can be used to ultimately separate the resulting thin fibrils of this invention from the remainder of the tissue.

The collagen fibers are desirably incubated with the antibodies to promote the biglycan disassociations. In one embodiment of this invention, the incubation of the antibodies and the collagen fibers is performed in a buffered solution. A particularly preferred buffered solution includes Tris Buffered Saline (TBS) (e.g., 0.15 M Tris, 0.05 M NaCl, pH-7.5).

The method of this invention can be applied generally to animal collagen. In one embodiment of this invention, sea lamprey notochord is a particularly preferred source of native type II collagen fibers for obtaining the thin fibrils of this invention. Lamprey notochord is also particularly useful as a model for studies of antibody effect on collagen type II fibrillar meshwork as lamprey notochord collagen fibrils and biglycan are essentially indistinguishable from those found in mammalian cartilage. The difference between notochord and cartilage is in the respective macrostructures. The specific arrangement of common ECM components as well as the introduction of tissue specific additional components gives rise to the different macrostructures. Notochord contains mostly collagen type II, the proteoglycan biglycan, and fibronectin, whereas cartilage in addition to these molecules also generally includes, without limitation, other proteoglycans (such as decorin and fibromodulin), glycoproteins (aggrecan and others), and collagens type I, IX, and XI.

The following describes the preparation of collagen fibrils from a sea lamprey according to one embodiment of this invention. An adult lamprey fish is desirably defrosted in cold water, as tissues from an air defrosted lamprey can become slightly dehydrated and hot water defrosting can cause protein denaturation. The lamprey is then cut longitudinally and the skin and muscles are carefully removed by gently cutting and pulling away in a tail-to-head direction. The notochord should remain in the sheaf during this procedure. In order to prevent dehydration, the notochord should be moistened with TBS frequently during the following dissection steps. TBS keeps the notochord in a physiological-like condition and does not affect proteoglycan interactions like phosphate buffered saline (PBS) can. PBS may cause conformational changes of certain proteoglycans (biglycan in particular), which in turn may influence their interactions with collagen. Next the sheaf is removed to open the spinal cord canal for removal of nerve tissue and fat. The notochord should be cut open longitudinally and the soft central/internal content is then removed.

Dehydration of the tissue can cause fiber/fibril shrinkage, which will have a dramatic affect on the fibril crystallinity (i.e. its native state), although the method may be able to proceed using dehydrated samples, the samples will no longer truly represent the native state of the tissue. A humid environment can be used to avoid the shrinking, and using TBS to moisten the tissue every few seconds is preferred. Prepared notochord samples can be incubated in 0.5 mg/ml antibody solution in TBS (approximately 0.5 ml) for 1 hour at 4° C., than gently washed with TBS (e.g., twice at a 15 min interval) and stored in TBS at 4° C. prior to data collection and/or use of the collagen material. It is important to note that the above temperature is not required for this procedure, as there was no difference noted between, for example, room temperature and 4° C. The lower temperature may be preferred to minimize possible bacteria growth.

The invention includes a collagen material formed from native collagen, such as harvested from tissues according to the method discussed above. In one embodiment, the collagen material of this invention is in the form of a thin fibril similar to or identical to the constituent fibril forming native collagen fibers. Desirably the collagen fibrils of this invention each have a width (i.e., the dimension perpendicular to the longitudinal dimension of a fibril) of about 11 to about 17 nanometers, and more desirably about 11.5 to about 12.5 nanometers. In one embodiment, the collagen fibrils obtained by the antibody treatment described above each have a width of about 12 nanometers. The thin fibrils of one embodiment of this invention are also substantially free of proteoglycan, particularly when the proteoglycans are removed by the antibody treatment of the original collagen fibers. The collagen fibrils can be stored in a buffered solution having a pH of about 7.0 to about 7.5 for later use.

The thin collagen fibrils of this invention can be used as building blocks to form new biomaterials and/or tissues. As discussed above, cartilage ECM contains primarily collagen type II fibrils, in combination with collagen types I, IX, and XI. Key non-collagenous molecules (chiefly proteoglycans), crucial for cartilage functions and properties (structural support, compression resistance, bone protection, etc) include biglycan, aggrecan, decorin, fibromodulin. In addition, fibronectin is important for cell-matrix attachment, motility, and chondrocytes differentiation.

In one embodiment of this invention, donor animal tissue rich in type II collagen undergoes the thin fibril depolymerization protocol described above. In summary, the tissue is homogenized, sonicated, and/or treated with 4M Guanidine chloride and/or spun down via centrifugation to ensure more complete depolymerization into thin fibrils. Antibody treatment will remove proteoglycans, which may be washed/dialyzed/spun out of the thin fibril preparation. These other ECM remnants are in pellet form after centrifuge (compressed by centrifugal induced pressure).

The thin fibrils after the purification will be aligned randomly and this architecture is quite different from native cartilage or the original donor tissue structure. In one embodiment of this invention, an extracellular matrix can be formed from the thin fibrils by adding biglycan, decorin, fibronectin, aggrecan, polyethylene glycol, or combinations thereof to the thin fibril collagen. The thin fibril collagen can also be used to form a new tissue, such as cartilage. Treatment of the thin fibril preparation in the buffered environment (TBS) with addition of other ECM molecules provides for tissue construction (biglycan and decorin are highly involved in fibrillogenesis, aggrecan is important for cartilage stability and mechanical functions), will allow the construction of model tissue scaffold/infrastructure for cellular seeding to form new tissue.

When donor tissues are transplanted into patient (joint reconstruction surgeries), they typically integrate poorly into cartilage. Host chondrocytes do not readily move into new tissue, so the implant will remain alien. The methods and biomaterials and/or tissues of this invention can be used to make tissue integration more successful, which will speed up healing process and improve joint conditions. In addition, using a donor tissue, or its extraceullar matrix components, from non-human sources is expected to significantly improve the supply of transplant connective tissue. In one embodiment of this invention the collagen material is used as or to form a non-human scaffolding for tissue transplant, which then may be seeded with the recipient's own cells to facilitate tissue growth and integration without risk of rejection. The donor chondrocytes or bone marrow cells (which could come from the potential recipient of the new tissue to ensure host-donor compatibility) should be readily accessible and recognizable to the cells, since the animal conservation of collagen type II is high. It is principally the macromolecular organization of fibrillar collagen molecules such as type II collagen, that determines the type of tissue produced (dermis versus tendon versus bone for instance).

In one embodiment, the method essentially takes one form of native type II collagen organization, de-constructs it to the type II collagen fibrils, and then reconstitutes the fibril collagen material into a scaffolding form recognizable to cartilage cells to form a new tissue through the use of select non-collagen ECM components with collagen II thin fibrils. Furthermore, the density and shape of the cartilage can be controlled by centrifugation with different speed and medium in thin fibril preparation (for example, to include some thicker fibrils) and the composition and ratio of the non-collagenous ECM molecules added to the reconstitution phase. The shape of the cartilage tissue can be also regulated by the type of micro-centrifuge tubes. The biomaterials and/or tissues formed from the fibril collagen can be used for wound treatment, tissue seeding, organogenesis and similar processes.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

In this example, transmission electron microscopy (TEM) is used to demonstrate the production of the thin fibril collagen material of this invention. In TEM an electron beam is emitted from a thin tungsten filament (thermionic emission) and accelerated by an electric potential to penetrate a sample and interact with the sample. As a result, some electrons are scattered, some are absorbed and some transmitted through the specimen. The transmitted signal is focused and magnified by additional apparatus and detected by CCD camera or other imaging apparatus.

In this Example intact collagen type II fibers from lamprey notochord are compared with bovine articular cartilage (collagen type II) and rat-tail tendon (collagen type I) fibers. By treating samples with antibodies, which label the proteoglycans still attached to collagen molecules within the fibers, it is possible to get a better idea about collagen—ECM interactions.

To prepare the samples, rat-tail tendons were pulled out from the tail and the notochord was extracted from defrosted sea lamprey. The tissues were separated into samples and stored in Phosphate Buffered Saline (PBS) or in Tris Buffer Saline (TBS) at 4° C. for 2 hours for native condition visualization and for antibody interaction experiments. The samples were then dissected into smaller pieces (1×1×2 mm) and stored in 0.5 ml of buffer at 4° C. Biglycan/decorin antibodies (human, rat, bovine, dog) were provided by NOVUS, frozen in TBS, and were defrosted before the experiment.

Tissues stored in TBS were transferred to vials with the antibody solution and incubated there for 2 hours at 4° C. Then the treated samples were washed in TBS and stored in 0.5 ml of TBS each at 4° C. overnight. Additional preparations were done for a control. The samples initially stored in PBS were washed in TBS and stored in TBS or introduced to antibody solution, and then washed and stored in TBS at 4° C. overnight. For imaging, the tissues were fixed, embedded and sectioned at the University of Chicago Microscopy Center to provide samples according to the TEM protocols.

FIG. 1. is the obtained TEM image of rat-tail tendon sample (collagen type I) without antibody treatment. FIG. 2 is the obtained TEM image of lamprey notochord fibers without antibody treatment. FIG. 3 is the obtained TEM image of bovine articular cartilage collagen type II fibrils (TBS) without antibody treatment.

As seen in FIGS. 1-3, collagen fibers have a typical pattern for fixed tissues: black and white bands with approximately 64 nm period (i.e. the D-period is shortened during fixation and embedding). The image of the lamprey notochord collagen type II fibers in FIG. 2 does not show any detectable difference from the fibers from tissues of a mammal (bovine) in FIG. 3. Both fibers have the same diameter of about 30-35 nm and the typical positive staining pattern. The lamprey notochord fibers of FIG. 2 appear to have a very specific cell distribution and most of them were mechanically removed during preparation, whereas cartilage cells are embedded in the collagen meshwork and can be seen through out the whole tissue in FIG. 3.

Figure 6:
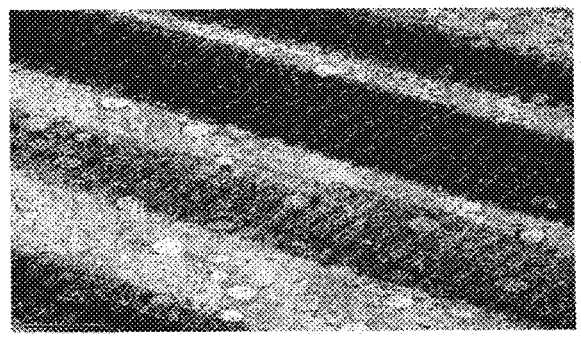

FIG. 4 is a TEM image of the lamprey tissues after antibody treatment. The difference in size between the fibrils in FIG. 4 and the native fibers in FIG. 2 is clear. The fibrils in FIG. 4 are much thinner at about 12 nm in diameter, and also the ECM is significantly less ordered. FIG. 5 shows that the antibody treated bovine cartilage was not affected to the extent of the lamprey fibers, but FIG. 5 also shows the thin fibrils and disrupted fibers in the presence of the antibody. The difference in the scale of the antibody effect on the lamprey versus bovine tissues can be explained due to the higher and more diverse cartilage proteoglycan composition found in the bovine cartilage. Although it should be noted, the presence of the effect of the antibody in terms of causing type II fibrils to become disassociated from their fibril bundles was the same between both tissues. As a comparison, FIG. 6 shows that the type I rat-tail tendon tissues did not show any significant changes after this particular antibody treatment.

FIGS. 2-5 illustrate the effect of biglycan antibody on collagen type II fibers in these tissues. The antibodies interacted with the biglycan molecules on the fiber surface and this interaction disrupted the bonding between the biglycan and the collagen molecules, which was crucial for holding the fibrils together and regulation of the collagen fiber diameter.

A similar phenomenon was observed in notochord samples stored in PBS, but not for those stored in TBS or stored in PBS for only a short time and then washed and stored in TBS. Studies of biglycan and decorin stability in different buffer systems has revealed that biglycan is more sensitive to pH and temperature changes and it is also less stable in PBS, than in other buffers compared to decorin. Therefore long exposure to PBS or interaction with the biglycan/decorin antibody can cause the conformational changes of biglycan ligated to collagen, whereas decorin appears to remains stable under the same conditions (as inferred from the fact that fibrils and fibers in rat-tail tendons appear to remain intact and unchanged from the native state as determined by TEM and X-ray diffraction). It is known that the interaction between collagen and cartilage proteoglycans strongly depends on their conformation. Thus, even small changes are enough to destroy the connection between biglycan and collagen molecules and the collagen fiber becomes loosened and vulnerable to dissociation into its constituent smaller fibrils, but not into single collagen molecules, due to existing lysine-hydroxylysine cross-links (i.e., fibril structure is established through collagen-collagen interactions).

Rat-tail tendon and bovine articular cartilage contains biglycan and decorin as well as other ECM molecules, which regulate fibrillogenesis, fiber diameter, support fibers, and give the tissue specific mechanical properties. Rat-tail tendon has a relatively small amount of biglycan, whereas the decorin concentration is relatively large (about 80% decorin and about 20% of all other proteoglycans). Cartilage and meniscus contain more biglycan than decorin and the ratio changes from zone to zone. The superficial zone contains about 32% of decorin and 38% of biglycan of all proteoglycan content, the inner deep zone contains about 23% of decorin and 53% of biglycan of all proteoglycans, and middle zone has 28% of decorin and 52% of biglycan of all proteoglycans. As a result these tissues will be more resistant to even 12 hours of antibody treatment, due to presence of decorin, which seems to be stable in the presence of this particular antibody (this antibody has higher affinity to biglycan, than decorin). Longer exposure of cartilage tissues to biglycan antibodies has a stronger effect on cartilage collagen fiber disassociation, as antibodies need more time to penetrate to deeper layers, where biglycan is predominant.

It is important to mention that the decorin interaction with collagen type I is much stronger than with type II, but the biglycan interaction with collagen type I is much weaker than interaction with collagen type II. And the antibody, which was used in these experiments, has higher affinity to biglycan than to decorin. This also explains the rat-tail tendon collagen type I fibers resistance to the antibody treatment.

This Example illustrates how the method of this invention can be used as a model for the mechanism of collagen matrix degradation by MMPs induced by autoimmunity. Collagen fibrils are assembled in such way that the MMP collagenase cleavage site is protected by the C-telopeptide in folded conformation Perumal, S., Antipova, O., and Orgel, J., "Collagen fibril architecture, domain organization, and triple-helical conformation govern its proteolysis," *Proc. Natl. Acad. Sci. U.S.A.* 105.8 (2008):2824-2829. This folded C-telopeptide corresponds to the X3 ridge in type I collagen, and appears to have an analogous structure in type II collagen as seen by AFM. The C-telopeptide is usually crosslinked covalently with neighboring collagen molecules that helps makes its conformation very stable. In order gain access to the MMP cleavage site, other proteases have to cleave the C-telopeptide first. This process is slow and MMP1 presence alone is not enough to destroy collagen fiber due to a very low number of available cleavage sites, if any. These results demonstrate that the biglycan antibody can induce the process of collagen fiber decomposition in cartilage-like tissues. Even a short, one-hour exposure of lamprey notochord to biglycan antibody completely altered the structure of the collagen matrix.

The antibody binds to the biglycan and cause conformation changes. This new conformation does not support the interaction with collagen fiber. The collagen and biglycan dissociate and collagen fiber (fibril bundle) starts its dissociation into smaller fibrils, supported only by collagen-collagen interactions. The thin collagen type II fibrils have a much more open surface, due to their smaller size and higher radius of curvature in comparison to thick fibers/type I fibrils. This may make these thin fibrils more accessible for collagenase binding, unwinding and cleavage, than when formed in the thick properly assembled fibers. Therefore, this altered collagen matrix is very fragile and readily and rapidly digested by proteases such as the MMPs.

The lamprey notochord has a rather simple composition (mostly collagen type II and biglycan) in comparison to mammalian cartilage, but this helps make it both an appealing and suitable model of mammalian systems for investigation of normal and pathological processes in cartilage. The examined interaction of biglycan antibodies with the notochord ECM can serve as a model for rheumatoid arthritis mechanism and has a direct potential for cure development investigations. The visualization of antibody-treated tissues under different conditions thus provides a model of autoimmune-induced rheumatoid arthritis, characterized by collagen matrix reformation and degradation, due to proteoglycan removal from the collagen fiber by biglycan antibody.

Figure 7:
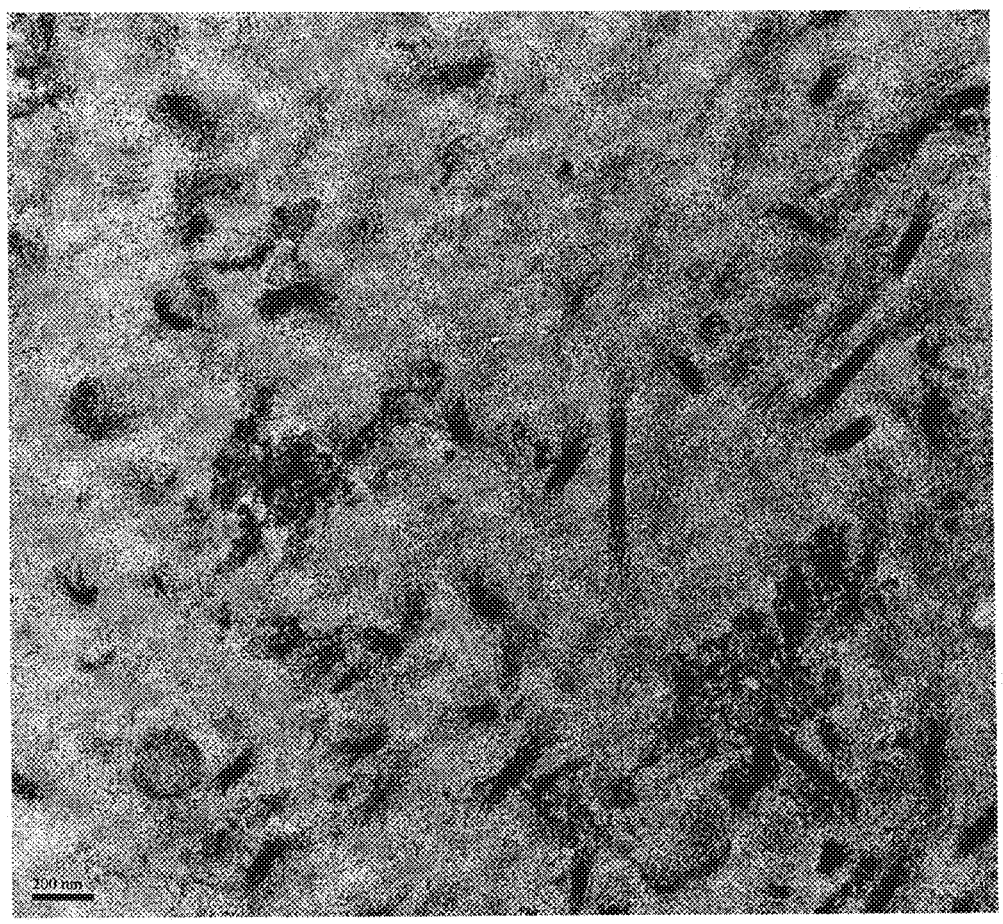
FIG. 7 is a TEM of an extracellular matrix according to one embodiment of this invention.

FIG. 7 illustrates an ECM made according to one embodiment of this invention. A piscine thin fibril preparation was made according to the method of this invention. The thin fibrils were incubated with the proteoglycan biglycan (mammalian) for approximately 18 hours at 4° C. in TBS buffer at pH 7-7.5. The biglycan was added to the thin fibril preparation at a concentration of approximately 0.25 mg/ml. The original fibril preparation was verified by TEM and the preparation was verified again by TEM after incubation and showed formation of new fibril-bundles with an organization having the appearance of proto-cartilage.

Thus, the invention provides a collagen material in the form of a thin fibril generally free of fibril-bundling proteogylcan interactions, and a method for providing the thin fibril collagen material from native collagen fibers. The antibody treatment of this invention produces a useful model system for RA study, and gives rise to a basic unit of connective tissue that may then be harvested and used to develop novel biomaterials.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

---

---

What is claimed is:

1. A fibril collagen:
   wherein the fibril collagen is obtained by providing isolated collagen fibers, wherein the collagen fibers comprise native type II collagen fibers; and
   treating the collagen fibers with an antibody to obtain the thin collagen fibrils, wherein the antibody comprises an anti-biglycan antibody and the thin collagen fibrils have a diameter of about 11.5 to about 12.5 nanometers.

2. The fibril collagen of claim 1, wherein the native type II collagen fibers are removed from a source selected from the group consisting of cartilage, bones, intervertebral discs, inner ear, vitreous humour, dermis, notochord, and combinations thereof.

3. The fibril collagen of claim 1, wherein the native type II collagen fibers are removed from a source selected from the group consisting of lamprey notochord, bovine articular cartilage, and combinations thereof.

4. The fibril collagen of claim 1, wherein the native type II collagen fibers are obtained from *Petromyzon marinus*.

5. The fibril collagen of claim 1, wherein the fibril collagen is formed into extracellular matrices.

6. The fibril collagen of claim 1, wherein the fibril collagen is suitable for administration to patients in need thereof.

7. A fibril collagen model for disease pathology, the model comprising thin collagen fibrils obtained by:
   providing isolated collagen fibers, wherein the collagen fibers comprise native type II collagen fibers; and
   treating the collagen fibers with an antibody to obtain thin collagen fibrils, wherein the antibody comprises an anti-biglycan antibody and the thin collagen fibrils have a diameter of about 11.5 to about 12.5 nanometers.

8. The model of claim 7, wherein the disease pathology is rheumatoid arthritis.

9. The model of claim 7, wherein the collagen fibers are obtained from *Petromyzon marinus*.

* * * * *

SEQUENCE LISTING

```
<160> NUMBER OF SEQ ID NOS: 1

<210> SEQ ID NO 1
<211> LENGTH: 12
<212> TYPE: PRT
<213> ORGANISM: Capra aegagrus

<400> SEQUENCE: 1

Asp Arg Leu Ala Ile Gln Phe Gly Asn Tyr Lys Lys
1               5                   10
```